(12) United States Patent
Ikeda

(10) Patent No.: US 7,076,394 B2
(45) Date of Patent: Jul. 11, 2006

(54) METHOD AND DEVICE FOR INSPECTING AN OBJECT USING A TIME DELAY INTEGRATION SENSOR

(75) Inventor: Hiroyuki Ikeda, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 154 days.

(21) Appl. No.: 10/792,848

(22) Filed: Mar. 5, 2004

(65) Prior Publication Data

US 2004/0263829 A1   Dec. 30, 2004

(30) Foreign Application Priority Data

Mar. 11, 2003   (JP) ............................. 2003-065118

(51) Int. Cl.
*G01M 19/00* (2006.01)
(52) U.S. Cl. .................. 702/125; 702/84; 702/104; 702/108; 702/124; 324/750
(58) Field of Classification Search .................. 702/89, 702/125; 324/750, 751, 753
See application file for complete search history.

(56) References Cited

U.S. PATENT DOCUMENTS

| 6,365,897 | B1 * | 4/2002 | Hamashima et al. ........ 250/310 |
| 2002/0001759 | A1 * | 1/2002 | Ohashi et al. ................. 430/5 |
| 2004/0100629 | A1 * | 5/2004 | Stokowski et al. ...... 356/237.2 |

FOREIGN PATENT DOCUMENTS

JP   P 2002-22673   1/2002

\* cited by examiner

*Primary Examiner*—Marc S. Hoff
*Assistant Examiner*—Phuong Huynh
(74) *Attorney, Agent, or Firm*—Finnegan, Henderson, Farabow, Garrett & Dunner, L.L.P.

(57) ABSTRACT

A method for inspecting an object using a time delay integration sensor. A storage time of the time delay integration sensor is changed in response to a signal level of a signal outputted from the time delay integration sensor, and a scanning speed of a scan by the time delay integration sensor is changed in response to the signal level of the signal outputted from the time delay integration sensor. The object is then scanned using the time delay integration sensor to inspect the object under the changed storage time and the changed scanning speed.

20 Claims, 4 Drawing Sheets

METHOD AND DEVICE FOR INSPECTING AN OBJECT USING A TIME DELAY INTEGRATION SENSOR

CROSS REFERENCE TO RELATED APPLICATION

This application is based upon and claims the benefit of priority from prior Japanese Patent Application No. 2003-65118 filed on Mar. 11, 2003, the entire contents of which are incorporated herein by reference.

FIELD OF THE INVENTION

The present invention relates to a method and apparatus for inspecting an object. In particular, a method and apparatus to inspect an object, such as a mask for manufacturing semiconductor device, uses a Time Delay Integration (TDI) sensor.

DISCRIPTION OF THE RELATED ART

A TDI sensor may be used in an inspecting apparatus for obtaining an image or even a fine image.

The TDI sensor is provided with one-dimensional sensors (line sensors) arranged in parallel.

The principle of the TDI sensor is briefly explained next.

Electric charges stored by a first line sensor are transferred to a second line sensor adjacent to the first line sensor. The second line sensor transfers the sum of the transferred electric charges plus electric charges stored by the second line sensor, to a third line sensor adjacent to the second line sensor. Like this, the last line sensor outputs the accumulated electric charges.

After amplifying the accumulated electric charges, the TDI sensor outputs the amplified electric charges as sensor-data.

This TDI sensor has two merits.

First, the TDI sensor can obtain electric charges dozens of times of that obtained by a single line sensor, because the TDI sensor scans one object with plural line sensors and accumulates electric charges which are stored by each line sensor.

Second, the TDI sensor reduces random noises because the TDI sensor scans one object with plural sensors. Consequently, S/N ratio of the sensor-data improves.

When a light intensity of a light source deteriorates, a signal level outputted from the TDI sensor also decreases, which makes it difficult to inspect an object precisely.

When a sensitivity of the TDI sensor deteriorates, a signal level outputted from the TDI sensor also decreases, which makes it difficult to inspect an object precisely, too.

There are two ways to be taken in order to maintain the signal level for a precise inspection.

One is increasing a gain to amplify the accumulated electric charges.

The other is increasing an intensity of a light of a light source.

However, increasing the gain causes the deterioration of the S/N ratio. As a result, the inspection accuracy gets worse.

While, it is difficult to automatically change the light intensity of the light source. It takes long time to stabilize the light intensity after the changing.

The TDI sensor mentioned above is disclosed in Japanese Patent Publication No. 2002-22673.

SUMMARY OF THE INVENTION

One aspect of the present invention is a method for inspecting an object using a time delay integration sensor, the time delay integration sensor having a settable storage time and an output.

The method comprises changing the storage time in response to a signal level of a signal outputted from the time delay integration sensor, changing a scanning speed of a scan by the time delay integration sensor in response to the signal level of the signal outputted from the time delay integration sensor, and scanning the object using the time delay integration sensor with changed storage time and the changed scanning speed.

Another aspect of the present invention is a method for inspecting an object using a time delay integration sensor, the time delay integration sensor having a settable storage time and an output.

The method comprises selecting a category of object to be inspected, changing the storage time in response to the selected object category, changing a scanning speed of a scan by the time delay integration sensor in response to the selected object category, and scanning the object using the time delay integration sensor with the changed storage time and the changed scanning speed.

Further aspect of the present invention is a method for inspecting an object using a time delay integration sensor, the time delay integration sensor having a settable storage time and an output.

The method comprises selecting an inspection category to inspect the object, changing the storage time in response to the selected inspection category, changing a scanning speed of a scan by the time delay integration sensor in response to the selected inspection category, and scanning the object using the time delay integration sensor with the changed storage time and the changed scanning speed.

Further aspect of the present invention is an inspecting apparatus.

The apparatus comprises a light source to irradiate an object to be inspected with light, a time delay integration sensor to receive the light with which the object is irradiated and output a signal, a time delay integration sensor controller to control a storage time of the time delay integration sensor in response to a signal level of the signal outputted from the time delay integration sensor, and a scanning speed controller to control a scanning speed of the time delay integration sensor in response to the signal level of the signal outputted from the time delay integration sensor.

Further aspect of the present invention is a method for manufacturing a mask.

The method comprises fabricating the mask by forming a pattern on a substrate, inspecting the mask using a time delay integration sensor, the time delay integration sensor having a settable storage time and an output, the inspection comprising, changing a storage time of a time delay integration sensor in response to a signal level of a signal outputted from the time delay integration sensor, changing a scanning speed of a scan by the time delay integration sensor in response to the signal level of the signal outputted from the time delay integration sensor, and scanning the mask using the time delay integration sensor with changed storage time and the changed scanning speed.

Further aspect of the present invention is a method for manufacturing a semiconductor device.

The method comprises inspecting a mask using a time delay integration sensor, the time delay integration sensor having a settable storage time and an output, the inspection comprising, changing a storage time of a time delay integration sensor in response to a signal level of a signal outputted from the time delay integration sensor, changing a scanning speed of a scan by the time delay integration sensor in response to the signal level of the signal outputted from the time delay integration sensor, and scanning the mask using the time delay integration sensor with changed storage time and the changed scanning speed, transferring a pattern on the mask onto a semiconductor wafer, and processing the semiconductor wafer to complete the semiconductor device following the transfer.

DETAILED DESCRIPTION OF THE INVENTION

One embodiment of an inspecting apparatus using a TDI sensor in accordance with the present invention is described below with reference to FIGS. 1 to 7.

Figure 1:
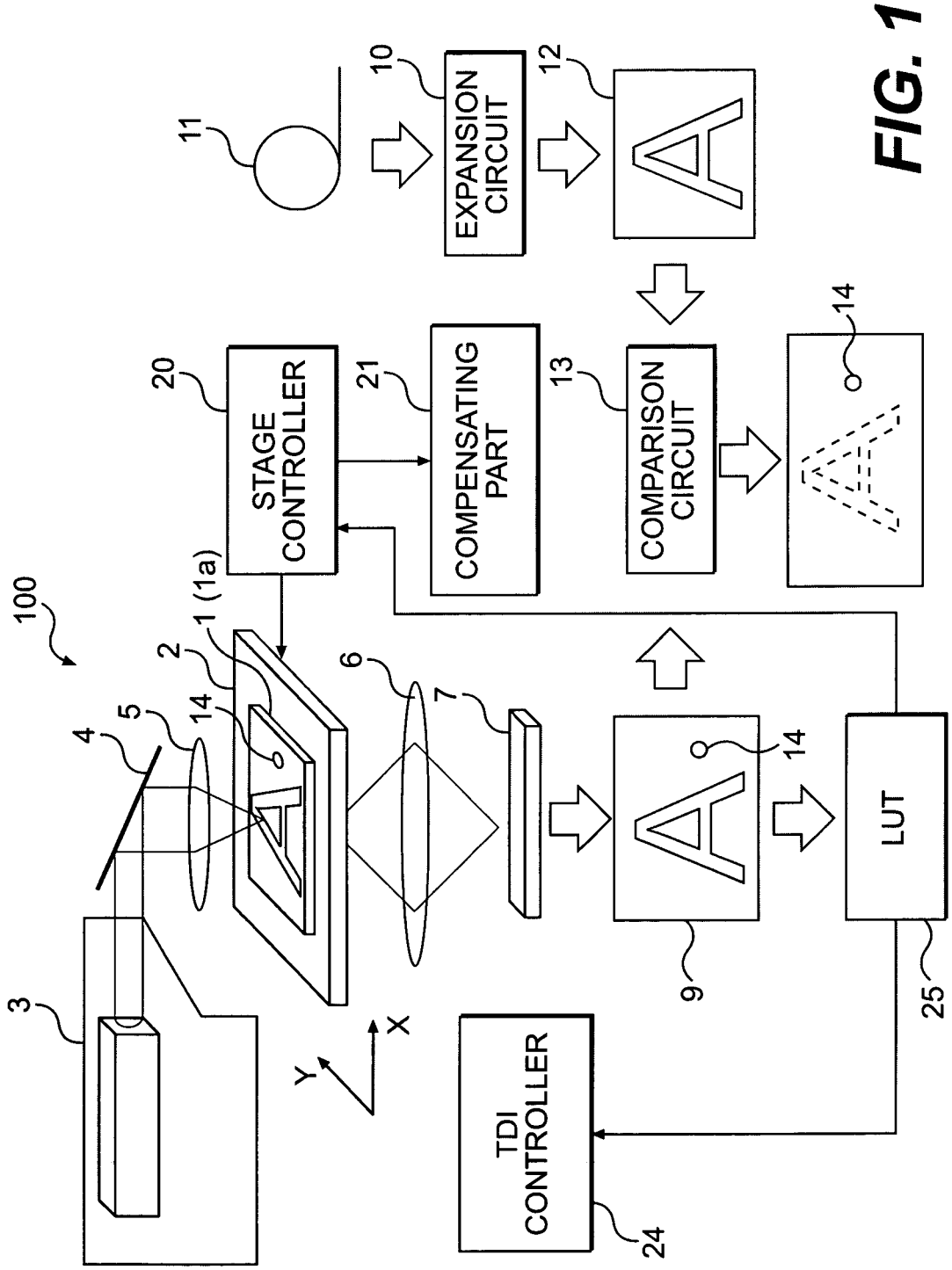
FIG. 1 is a schematic view of an embodiment of an inspecting apparatus.

FIG. 1 shows a schematic view of one embodiment of an inspecting apparatus 100. Inspecting apparatus 100 inspects a mask 1.

Inspecting apparatus 100 is provided with a laser apparatus 3, an X-Y stage 2, a stage controller 20 as a scanning speed controller for driving and controlling the X-Y stage 2, a TDI sensor 7, a TDI controller 24 for controlling the TDI sensor 7, a look-up table (LUT) 25, a compensating part 21, an expansion circuit 10, and a comparison circuit 13.

Laser apparatus 3 outputs a laser beam for irradiating mask 1.

A reflection mirror 4 and a focusing lens 5 are successively arranged along the optical path of the laser beam. The X-Y stage 2 which is movable in the X and Y directions and is arranged so that a laser beam focused by lens 5 focuses on the surface of the X-Y stage 2.

Stage controller 20 drives X-Y stage 2. Mask 1 to be inspected is set on X-Y stage 2.

An imaging lens 6 and the TDI sensor 7 are successively arranged along the optical path of the laser beam which passes through mask 1 and the X-Y stage 2. In order to change a magnifying capacity of the imaging lens 6, plural imaging lenses 6 are prepared (not shown). The TDI sensor 7 outputs a sensor-data 9 of the mask 1 by scanning the mask 1.

Comparison circuit 13 compares sensor-data 9 with a reference data 12 in order to judge whether or not, mask 1 has a defect.

Detailed description of the operation of TDI sensor 7 is explained next with reference to FIGS. 5 to 7.

Figure 5:
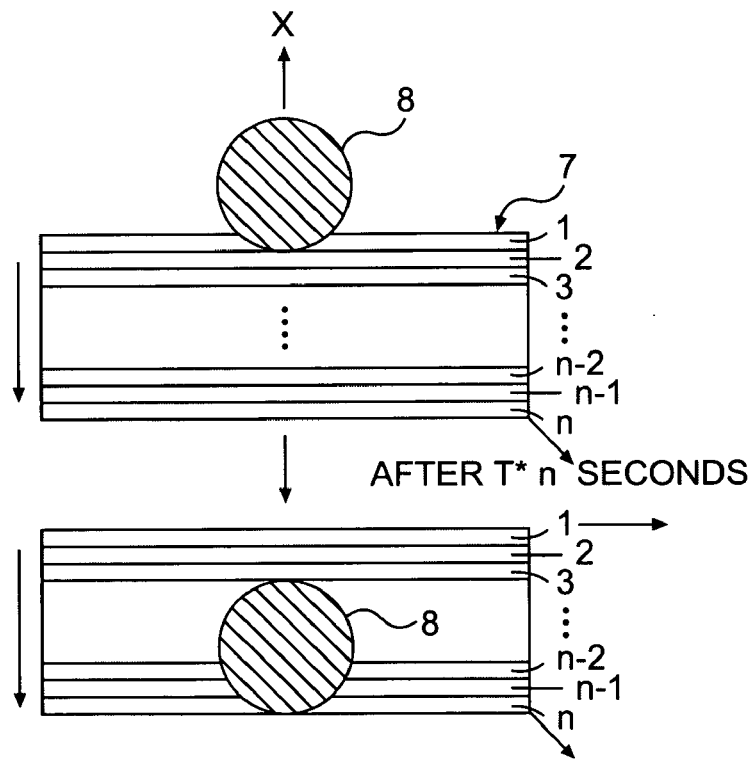
FIGS. 5 and 6 are drawings to explain an operation of a TDI sensor of the apparatus shown in FIG. 1.

As shown in FIG. 5, TDI sensor 7 is provided with multiple lines of line sensors arranged in parallel. Each line sensor is numbered in FIG. 5. The number of the line sensors is N, which means any number more than one. In this embodiment, the number of line sensors is 1024.

In order to obtain an image of a test object 8 with the TDI sensor 7, the TDI sensor 7 scans object 8 in the direction shown as an arrow X by moving X-Y stage 2, which direction is orthogonal to the longitudinal direction of the line sensors.

Figure 6:
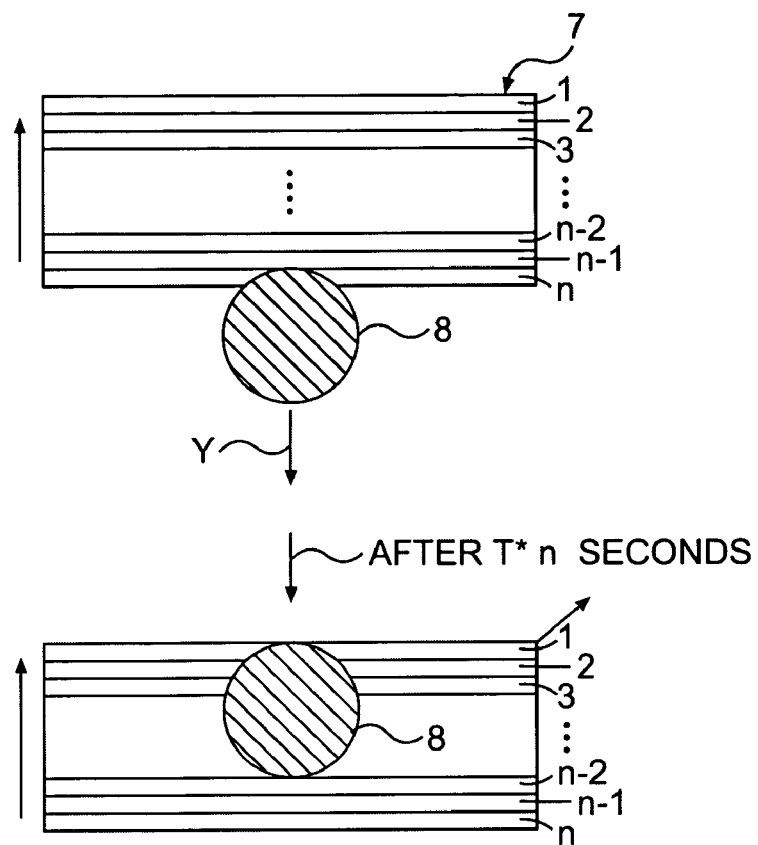

Electric charges stored in the first line sensor, which is numbered 1 in FIG. 6, are transferred to the second line sensor, which is numbered 2. Electric charges accumulated in the second line sensor, which electric charges are the sum of the transferred charges plus electric charge stored in the second line sensor, are transferred to the third line sensor. Like this, electric charges are accumulated and accumulated while electric charges are transferred from one line sensor to another adjacent line sensor. Finally, the last line sensor, number n in FIG. 6, outputs the accumulated electric charges.

When a scanning time (storage time) by a single line sensor is T seconds, the transfer of the electric charges from one line sensor to another line sensor is carried out every T seconds. It takes T*N seconds to scan a portion of test object 8 by all of the line sensors as shown in FIG. 5.

The TDI sensor 7 can change the direction of the accumulation. When TDI sensor 7 scans test object 8 in the reverse direction of an arrow Y as shown in FIG. 6, the electric charges stored in the last Nth line sensor are transferredtothe (N−1)th line sensor. The electric charges in the (N−1)th sensor, which electric charges are the sum of the transferred charges plus the electric charges stored in the (N−1) th sensor, are transferred to the (N−2) th sensor. Like this, electric charges are accumulated and accumulated while electric charges are transferred from one line sensor to another adjacent line sensor. Finally, the first line sensor outputs the accumulated electric charges.

The stage controller 20 drives and controls X-Y stage 2. As shown in FIG. 7, the TDI sensor 7 firstly scans the mask 1 in the −Y direction by moving the X-Y stage 2 with the stage controller 20. Secondly, the TDI sensor 7 scans the mask 1 in the +Y direction after a relative displacement of the TDI sensor 7 by the width of the line sensors in the X direction. The TDI sensor 7 scans the entire image of mask 1. The image is formed by imaging lens 6, so that TDI sensor 7 outputs sensor-data 9 of mask 1.

LUT 25 (FIG. 1) stores data referring to the relation between intensities of a light which passes through a transparent portion of the mask 1, and preferable scanning times of the line sensor of TDI sensor 7. It also stores data referring to the relation between the intensities and preferable movement speeds of the X-Y stage 2.

The LUT 25 is electrically connected to the TDI controller 24 and the stage controller 20.

The TDI controller 24 sets a scanning time of the TDI sensor 7 according to a scanning time determined by LUT 25. When the TDI controller 24 sets the scanning time of the TDI sensor 7, the transfer of electric charges from one line sensor to another line sensor is carried out every scanning time interval.

Stage controller 20 sets a movement speed of the X-Y stage 2 according to a movement speed determined by LUT 25.

Compensating part 21 is electrically connected to the stage controller 20. Compensating part 21 outputs a command to expansion circuit 10 to compensate the readout position of CAD (Computer Aided Design) data 11.

Figure 2A:
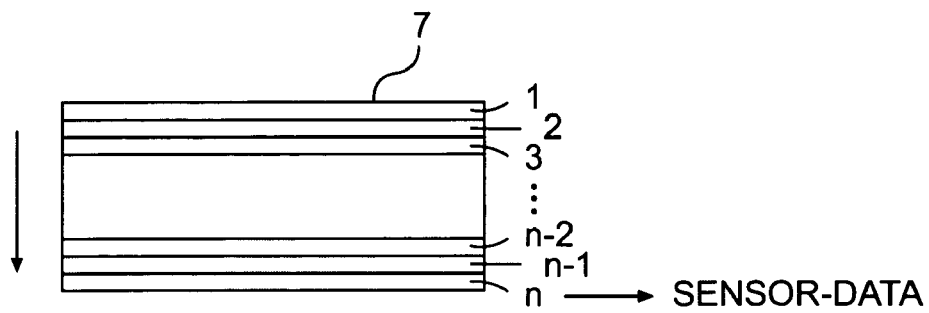
FIGS. 2A and 2B are drawings to explain a compensation of a readout position carried out by a compensation part of the apparatus shown in FIG. 1.

For example, when the TDI sensor 7 scans mask 1 in the Y direction as shown in FIG. 2A, the Nth line sensor outputs sensor-data 9. Expansion circuit 10 expands the CAD data 11 of a position where the Nth line sensor scans so that, comparison circuit 13 can compare sensor-data 9 of a position with reference data 12 of the same position.

Figure 2B:
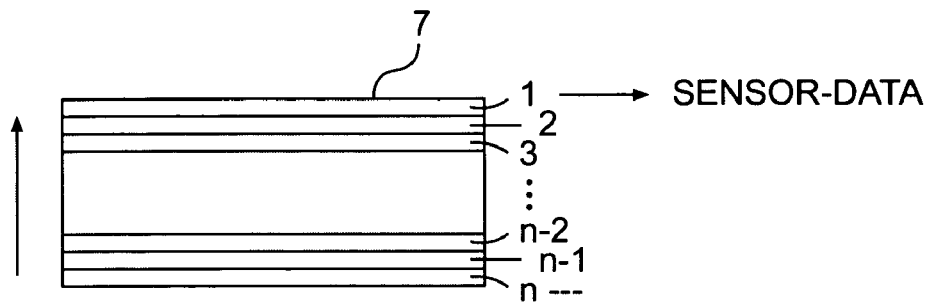

However, when the TDI sensor 7 scans the mask 1 in −Y direction as shown in FIG. 2B, the first line sensor outputs sensor-data 9. In order to compare sensor-data 9 outputted from the first line sensor with reference data 12 of the position where the first line sensor scans, it is necessary to compensate the readout position of CAD data 11.

Compensating part 21 commands the expansion circuit 10 to read CAD data 11 of the position where the first line sensor scans, when the TDI sensor 7 scans mask 1 in −Y direction. The stage controller 20 outputs the signal of the direction in which the X-Y stage 2 moves, to the compensating part 21.

The amount of the compensation depends on the number of line sensors, the width of the sensors, and the magnifying capacity of the imaging lens 6.

The compensating part 21 stores plural commands in which the amount of the compensation changes. The compensating part 21 selects one command according to the magnifying capacity of the imaging lens 6, and outputs the selected command to the expansion circuit 10.

The expansion circuit 10 expands CAD data 11 corresponding to the position where the Nth line sensor scans. However, the expansion circuit 10 expands CAD data 11 corresponding to the position where the first line sensor scans when the compensating part 21 outputs the command to the expansion circuit 10.

The expansion circuit 10 receives CAD data 11 from a database (not shown), and expands CAD data 11 in order to obtain reference data 12 every time the TDI sensor 7 scans another area, and outputs sensor-data 9 corresponding to the area just scanned.

Comparison circuit 13 compares sensor-data 9 obtained by the TDI sensor 7 with reference data 12 computed by the expansion circuit 10 every time the TDI sensor 7 scans a predetermined area, and outputs sensor-data corresponding to the area. Thereby, the mask 1 is inspected in real time.

According to one embodiment, the mask 1 is made of a glass substrate on which circuit patterns of chromium for manufacturing a semiconductor device are formed. The patterns are transferred to a resist film on a semiconductor substrate in a patterning process for manufacturing a semiconductor device.

Figure 3:
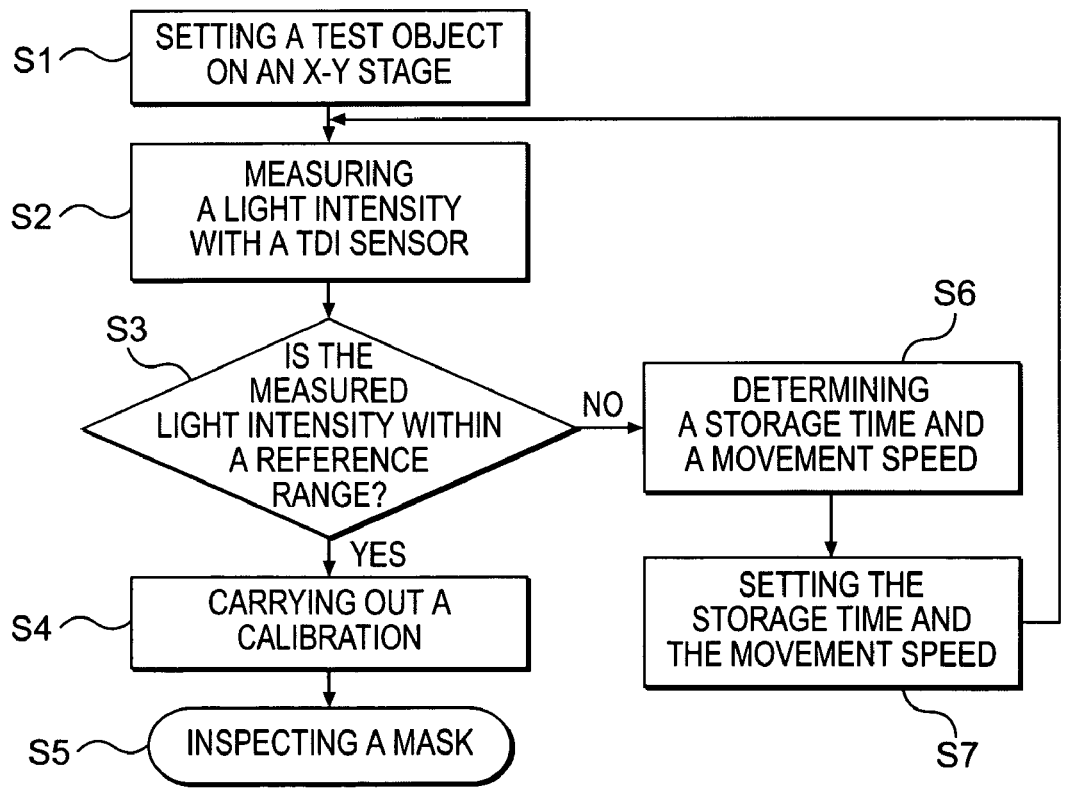
FIG. 3 is a flow chart showing a sequence of an inspection operated by the apparatus shown in FIG. 1.

An operation of inspecting apparatus 100 is explained next with reference to FIG. 3.

The TDI sensor 7 is calibrated before an inspection of the mask 1. If a deterioration of a signal level outputted from the TDI sensor 7 is found in the calibration step, the scanning time of the TDI sensor 7 and the movement speed of The X-Y table 2 are adjusted according to the LUT 25.

In step S1, the test object 1a on which a test pattern with a white portion (a transparent portion) and a black portion (a light-shielding portion) are formed is set on the X-Y stage 2.

In step S2, a laser beam emitted from laser apparatus 3 irradiates the test object 1a so that the TDI sensor 7 senses the laser beam which passes through the white portion. Thereby, a signal level outputted from the TDI sensor 7 in terms of the light intensity of the laser beam is measured.

In step S3, it is judged whether or not the light intensity is within a predetermined reference range.

In step S4, when the light intensity is within the range, a calibration of the TDI sensor 7 is carried out.

In step S5, after the calibration, the mask 1 to be inspected is set on the X-Y stage 2 after removing the test object 1a. Then, the mask 1 is inspected.

If the light intensity is not within the reference range, the preferable scanning time of the TDI sensor 7 and the preferable movement speed of the X-Y stage 2 are determined according to the LUT 25, in step S6.

In step S7, the TDI controller 24 sets the determined scanning time as a scanning time of the TDI sensor 7, and the stage controller 20 sets the movement speed of the X-Y stage 2.

Then, steps S2 and S3 are repeated. A light intensity which passes through a white portion of the test object 1a, is measured again. When the light intensity is within the reference range, calibration is carried out in step S4. After the calibration, inspecting apparatus 100 inspects the mask 1.

Therefore, even though a light intensity of the light source deteriorates, the signal outputted from the TDI sensor 7 is prevented from deteriorating by changing a scanning time of the TDI sensor 7 and a movement speed of the X-Y stage 2. Thus, the S/N ratio of signal outputted from the TDI sensor 7 does not deteriorate relative to increasing in the gain for amplifying the signal.

Some inspections need a high intensity of a light. For example, an inspection using a reflected light needs high intensity because the light intensity of reflected light is weaker than that of direct light.

In one modification of the embodiment above, the scanning time of the TDI sensor 7 is changed according to a type of inspection instead of increasing the light intensity of a light source. The LUT 25 stores data on the relationships between preferable scanning times and types of inspection, and data on the relationships between the preferable movement speeds of the X-Y stage 2 and types of inspection.

Figure 4:
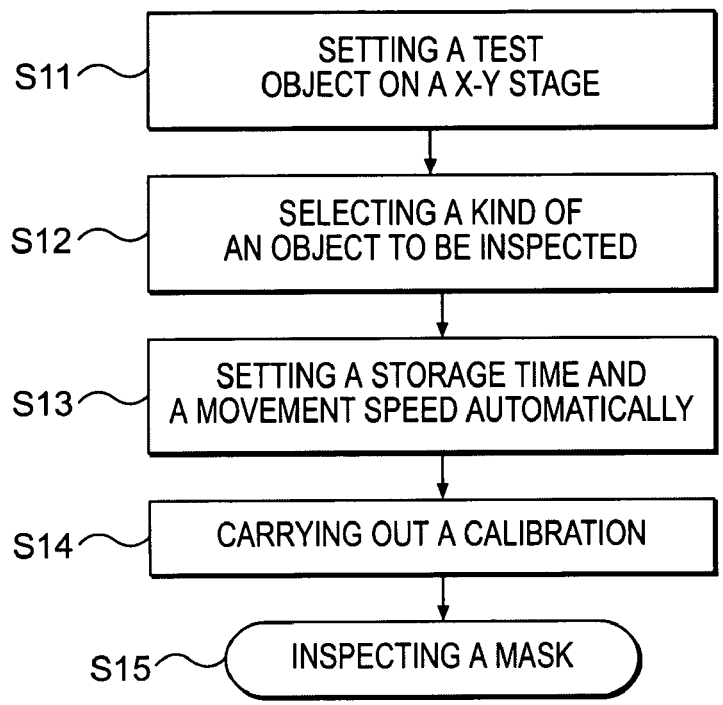
FIG. 4 is a flow chart showing a sequence of an inspection as one modification of the embodiment shown in FIG. 3.

FIG. 4 shows a flowchart of the operation in order to change the scanning time of the TDI sensor 7 and the movement speed of The X-Y table 2.

In step S11, the test object 1a on which a white pattern and a black pattern are formed is set on the X-Y stage 2.

Instep S12, a type of inspection is determined (selected).

In step S13, the TDI controller 24 automatically sets the scanning time of the TDI sensor 7, which scanning time is determined by the LUT 25 according to the type of an inspection. The stage controller 20 sets the movement speed of the X-Y stage 2, which is determinedby the LUT 25 according to the type of the inspection.

In step s14, the TDI sensor 7 is calibrated.

In step S15, apparatus 100 inspects the mask 1.

An inspection of the mask 1 is explained next.

Laser apparatus 3 emits a laser beam. The laser beam irradiates the mask 1 via reflection mirror 4 and focus lens 5. The laser beam which passes the mask 1 forms an image on the TDI sensor 7 by the forming lens 8.

The X-Y stage 2 moves the mask 1 so that the TDI sensor 7 scans all of the mask 1.

Figure 7:
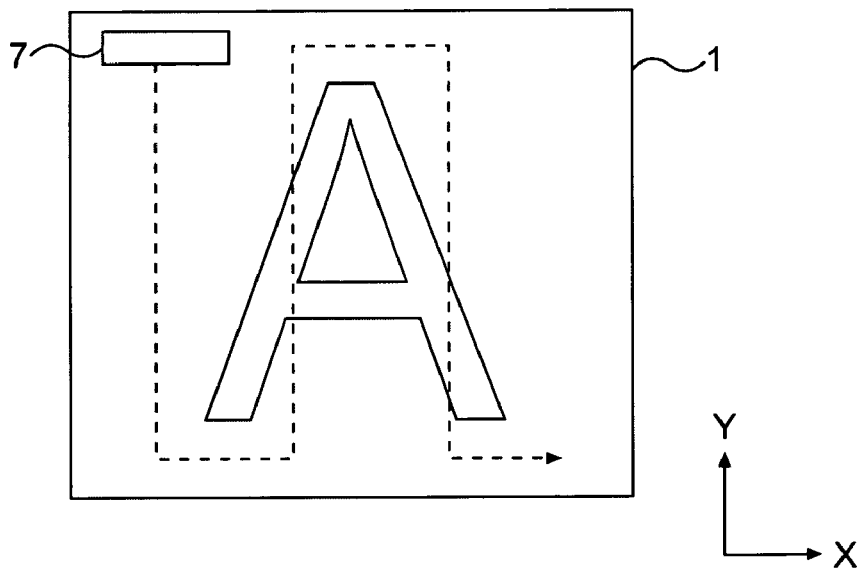
FIG. 7 is a drawing which shows a route of a scan by a TDI sensor of the apparatus shown in FIG. 1.

A detailed description of the relative movement between the mask 1 and the TDI sensor 7 follows next with reference to FIG. 7.

Firstly, the TDI sensor 7 scans the mask 1 in the −Y direction. Then, the mask 1 moves in +X direction relative to the TDI sensor 7 by the longitudinal width of the TDI sensor 7. The TDI sensor 7 then scans the mask 1 in the +Y direction. Like this, the TDI sensor 7 scans all of the mask 1.

The TDI sensor 7 outputs sensor-data 9 of the image of the mask 1 every time the electric charges accumulated by all N line sensors are outputted by the 1st or the last line sensors.

When the TDI sensor 7 scans all of the mask 1, all sensor-data 7 corresponding to the all of the mask 1 is obtained.

When the TDI sensor 7 scans the mask 1 in −Y direction, the compensating part 21 commands the expansion circuit 10 to expand CAD data 11 of the position where the Nth line sensor scans so that reference data 12 of the position where the Nth line sensor scans is obtained.

When the TDI sensor 7 scans the mask 1 in +Y direction, the compensating part 21 outputs a command based on the signal from the stage controller 20. The compensating part 21 commands the expansion circuit 10 to expand CAD data 11 of the position where the first line sensor of the TDI sensor 7 scans so that reference data 12 of the position where the first line sensor scans is obtained.

Comparison circuit 13 compares sensor-data 9 with reference data 12 every time sensor-data 9 is obtained.

Thus, defect inspection of the mask 1 is carried out in real time.

Even if the scanning direction of the TDI sensor 7 changes, the compensating part 21 compensates the displacement of the position of which the expansion circuit 10 expands CAD data 11.

Defect inspection with less error is carried out.

Consequently, a mask with fewer defects is manufactured with the mask inspection method mentioned above.

In the embodiment above, the scanning time of the TDI sensor 7 is changed instead of changing the gain of amplifying the signals. Thus, inspection accuracy may be maintained without decreasing the S/N ratio of the signals.

In addition, the LUT 25 stores a data referring to the relation between types of inspection and the scanning times of the TDI sensor 7. Thus, many types of inspection may be carried out. For example, it is possible to inspect a test object by refection light.

Instead of the type of the inspection, it is possible to determine the storage time and the scanning time according to the kind of the object to be inspected. For example, when an object to be inspected transmits light less than other objects, the storage time can be set longer and the movement speed can be set slower. While an object to be inspected transmits light more than other objects, the storage time can be set shorter and the movement speed can be set faster.

The TDI sensor 7 can be moved in order to change scanning speed of a scan by the TDI sensor 7 instead of moving the X-Y stage 2.

Numerous modifications of the present invention are possible in light of the above teachings. It is therefore to be understood that, within the scope of the appended claims, the present invention can be practiced in a manner other than as specifically described herein.

What is claimed is:

1. A method for inspecting an object using a time delay integration sensor, the time delay integration sensor having a settable storage time and an output, the method comprising:
changing the storage time in response to a signal level of a signal outputted from the time delay integration sensor;
changing a scanning speed of a scan by the time delay integration sensor in response to the signal level of the signal outputted from the time delay integration sensor; and
scanning the object using the time delay integration sensor with changed storage time and the changed scanning speed.

2. A method for inspecting an object using a time delay integration sensor according to claim 1, further comprising measuring a signal level of a signal outputted from the time delay integration sensor, wherein the step of changing the storage time includes changing the storage time of the time delay integration sensor according to the measured signal, and the step of changing the scanning speed includes changing the scanning speed of the scan according to the measured signal.

3. A method for inspecting an object using a time delay integration sensor according to claim 1, wherein the step of changing the storage time includes increasing the storage time when the signal level is smaller than a reference value and the step of changing the scanning speed includes decreasing the scanning speed when the signal level is smaller than the reference value.

4. A method for inspecting an object using a time delay integration sensor according to claim 1, wherein the step of changing the storage time includes decreasing the storage time when the signal level is larger than a reference value and the step of changing the scanning speed includes increasing the scanning speed when the signal level is larger than the reference value.

5. A method for inspecting an object according to claim 1, wherein the object is a mask for manufacturing a semiconductor device.

6. A method for inspecting an object according to claim 1, further comprising inspecting the object by comparing sensor-data with reference data, the sensor-data being outputted from the time delay integration sensor during the scanning step.

7. A method for inspecting an object according to claim 1, wherein relations, between the storage time and the signal level, between the scanning speed and the signal level, are stored in a memory.

8. A method for inspecting an object according to claim 1, wherein the step of scanning the object includes receiving light reflected off the object.

9. A method for inspecting an object according to claim 1, wherein the step of scanning the object includes scanning the object by receiving a light which passes through a transparent portion of the object.

10. A method for inspecting an object according to claim 1, wherein the step of changing the scanning speed includes changing a stage movement speed of an X-Y stage on which the object is set, and scanning the object includes scanning the object by moving the X-Y stage according to the changed stage movement speed.

11. A method for inspecting an object using a time delay integration sensor, the time delay integration sensor having a settable storage time and an output, the method comprising:
selecting a category of object to be inspected;
changing the storage time in response to the selected object category;
changing a scanning speed of a scan by the time delay integration sensor in response to the selected object category; and
scanning the object using the time delay integration sensor with the changed storage time and the changed scanning speed.

12. A method for inspecting an object using a time delay integration sensor, the time delay integration sensor having a settable storage time and an output, comprising:

selecting an inspection category to inspect the object;

changing the storage time in response to the selected inspection category;

changing a scanning speed of a scan by the time delay integration sensor in response to the selected inspection category; and scanning the object using the time delay integration sensor with the changed storage time and the changed scanning speed.

13. An inspecting apparatus, comprising:

a light source to irradiate an object to be inspected with light;

a time delay integration sensor to receive the light with which the object is irradiated and output a signal;

a time delay integration sensor controller to control a storage time of the time delay integration sensor in response to a signal level of the signal outputted from the time delay integration sensor; and a scanning speed controller to control a scanning speed of the time delay integration sensor in response to the signal level of the signal outputted from the time delay integration sensor.

14. An inspecting apparatus according to claim 13, wherein the time delay integration sensor controller is configured to control the storage time in response to the signal level outputted from the time delay integration sensor and the scanning speed controller is further configured to control the scanning speed in response to the signal level of the signal outputted from the time delay integration sensor.

15. An inspecting apparatus according to claim 13, wherein the time delay integration sensor controller is configured to increase the storage time when the signal level is smaller than a reference value, and wherein the scanning speed controller is configured to decrease the scanning speed when the signal level is smaller than the reference value.

16. An inspecting apparatus according to claim 13, wherein the time delay integration sensor controller is configured to decrease the storage time when the signal level is larger than a reference value, and wherein the scanning speed controller is configured to increase the scanning speed when the signal level is larger than the reference value.

17. An inspecting apparatus according to claim 13, wherein the object is a mask for manufacturing a semiconductor device.

18. An inspecting apparatus according to claim 13, further comprising a comparison circuit which compares a sensor-data with reference data, wherein the sensor-data is outputted from the time delay integration sensor.

19. An inspecting apparatus according to claim 13, further comprising a memory storing relationships, between the storage time and the signal level, between the scanning speed and the signal level.

20. An inspecting apparatus according to claim 13, wherein the time delay integration sensor is configured to receive light reflected off the object.

* * * * *